(12) United States Patent
Frigg et al.

(10) Patent No.: US 7,850,690 B2
(45) Date of Patent: *Dec. 14, 2010

(54) DEVICE FOR THE TREATMENT OF FEMORAL FRACTURES

(75) Inventors: Robert Frigg, Bettlach (CH); Eric Hattler, Solothurn (CH); Walter Widmer, Oberdorf (CH); Elena Barrios, Port (CH); Stephan Küppers, Derendingen (CH)

(73) Assignee: Synthes USA, LLC, West Chester, PA (US)

( * ) Notice: Subject to any disclaimer, the term of this patent is extended or adjusted under 35 U.S.C. 154(b) by 1118 days.

This patent is subject to a terminal disclaimer.

(21) Appl. No.: 11/378,916

(22) Filed: Mar. 17, 2006

(65) Prior Publication Data

US 2006/0241604 A1    Oct. 26, 2006

Related U.S. Application Data

(63) Continuation of application No. PCT/CH03/00630, filed on Sep. 18, 2003.

(51) Int. Cl.
*A61B 17/76*    (2006.01)
(52) U.S. Cl. .......................................... 606/67; 606/64
(58) Field of Classification Search ............. 606/62–68, 606/98, 99; 623/23.11, 23.14, 23.15, 23.19, 623/23.21, 23.22, 23.23, 23.26, 23.27, 22.4–23.38; 411/383, 384
See application file for complete search history.

(56) References Cited

U.S. PATENT DOCUMENTS

| | | | | |
|---|---|---|---|---|
| 4,432,358 A | * | 2/1984 | Fixel | 606/66 |
| 4,733,654 A | * | 3/1988 | Marino | 606/64 |
| 5,032,125 A | * | 7/1991 | Durham et al. | 606/62 |
| 5,454,813 A | * | 10/1995 | Lawes | 606/62 |
| 5,902,303 A | * | 5/1999 | Eckhof et al. | 606/60 |
| 6,139,552 A | * | 10/2000 | Horiuchi | 606/88 |
| 6,221,074 B1 | * | 4/2001 | Cole et al. | 606/62 |
| 6,235,031 B1 | * | 5/2001 | Hodgeman et al. | 606/64 |

(Continued)

FOREIGN PATENT DOCUMENTS

DE    87 01 164    6/1987

(Continued)

*Primary Examiner*—Eduardo C Robert
*Assistant Examiner*—Jerry Cumberledge
(74) *Attorney, Agent, or Firm*—Fay Kaplun & Marcin, LLP

(57) ABSTRACT

A femoral fracture treatment device including: an intramedullary pin (1) with a central longitudinal axis (2) and a passage (5) of non-circular cross-section (6) through a proximal portion (4) of the pin oblique to the longitudinal axis (2), a sliding sleeve (10) configured to pass through the non-circular passage (5), a longitudinal bone fixing element (20) having a head portion (22) with fixing means (23) for engaging the femoral head and a shaft (24) that may be coaxially introduced into the sliding sleeve (10). Both an external jacket surface (14) of the sliding sleeve (10) and an internal jacket surface (15) of the sliding sleeve (10) have non-circular cross-sections at least in a partial section. The shaft (24) is rotatably mounted in the longitudinal bore (13) of the sliding sleeve (10), and locking means are provided at the free end (27) of the shaft (24), such that rotation of the longitudinal bone fixing element (20) relative to the sliding sleeve (10) can be optionally locked or released.

20 Claims, 6 Drawing Sheets

U.S. PATENT DOCUMENTS

| | | | |
|---|---|---|---|
| 6,248,095 B1 * | 6/2001 | Giambattista et al. | 604/207 |
| 6,423,066 B1 | 7/2002 | Harder et al. | |
| 6,443,954 B1 * | 9/2002 | Bramlet et al. | 606/62 |
| 6,468,278 B1 * | 10/2002 | Muckter | 606/291 |
| 2002/0143333 A1 * | 10/2002 | von Hoffmann et al. | 606/67 |
| 2002/0156473 A1 | 10/2002 | Bramlet et al. | |
| 2002/0173792 A1 * | 11/2002 | Severns et al. | 606/62 |
| 2003/0068210 A1 * | 4/2003 | Pountney | 411/384 |
| 2003/0074000 A1 * | 4/2003 | Roth et al. | 606/62 |
| 2005/0010223 A1 * | 1/2005 | Gotfried | 606/62 |
| 2006/0149247 A1 * | 7/2006 | Frigg et al. | 606/64 |
| 2006/0155281 A1 * | 7/2006 | Kaup et al. | 606/65 |
| 2006/0241606 A1 * | 10/2006 | Vachtenberg et al. | 606/65 |

FOREIGN PATENT DOCUMENTS

| | | | |
|---|---|---|---|
| DE | 19829228 C1 | * | 10/1999 |
| JP | 09220235 A | * | 8/1997 |
| JP | 2001025471 A | * | 1/2001 |
| JP | 2002065687 A | * | 3/2002 |
| WO | 03/028567 | | 4/2003 |

* cited by examiner

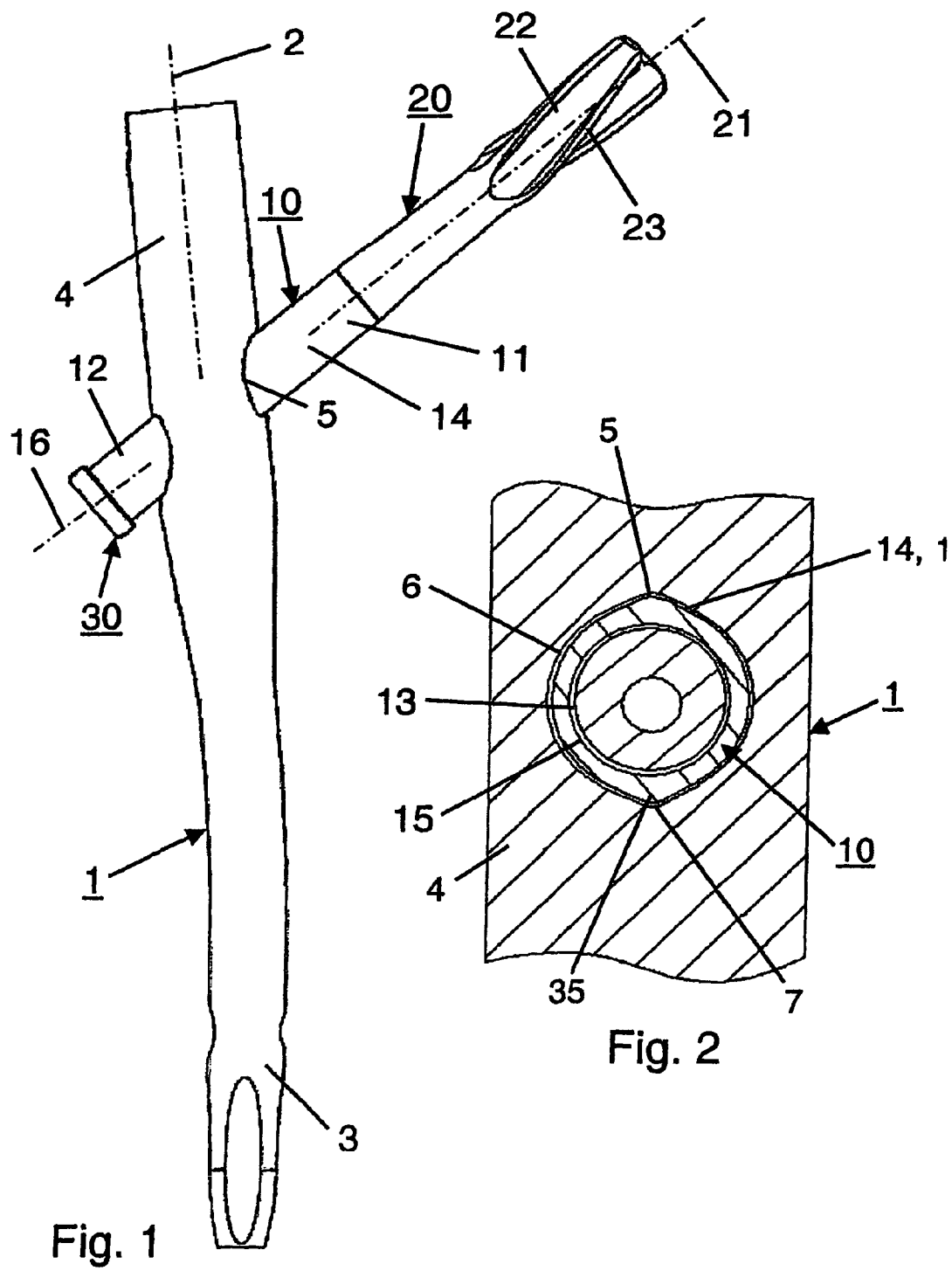

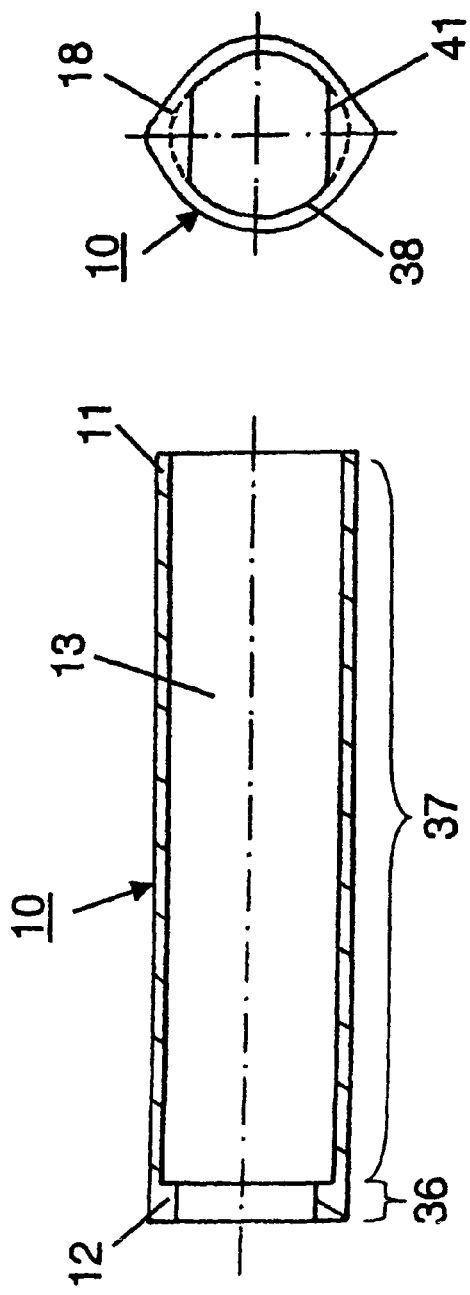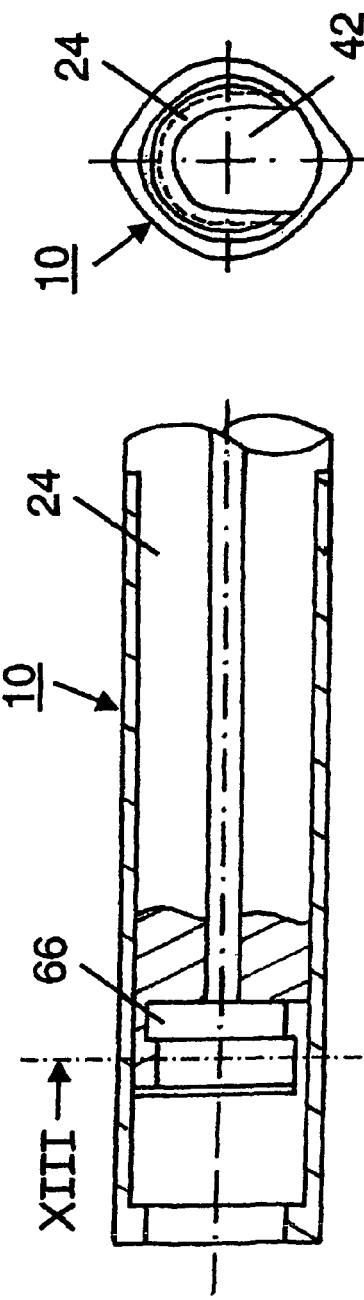

DEVICE FOR THE TREATMENT OF FEMORAL FRACTURES

RELATED APPLICATION DATA

The present application is a continuation of, and claims priority under 35 U.S.C. §120 to, International Application No. PCT/CH2003/000630, filed Sep. 18, 2003, the entire content of which is expressly incorporated herein by reference thereto.

FIELD OF INVENTION

The invention concerns a device for the treatment of femoral fractures.

BACKGROUND OF THE INVENTION

Devices, whereby a securing of the femoral head against rotation is attempted by a single hip screw, i.e. a longitudinal bone fixing means, are already known. From EP 0 441 577, for example, a device is known that has a sleeve accommodating the hip screw in a sliding manner, while the sleeve can be secured against rotation in the intramedullary pin by a locking screw proximally introduced into the intramedullary pin. The shaft of the hip screw and the bore of the sleeve are, however, not circular, so that the hip screw cannot rotate in the sleeve. However, during the introduction into the head of the femur the hip screw has to be able to rotate. For this reason during implantation the hip screw has to be inserted first and the sliding sleeve only afterwards. There is further the danger that the hip screw moves medially when a compression screw is not additionally employed. A further disadvantage is, that the locking screw has to be introduced from above (cranially) into the intramedullary pin, representing a further operating procedure. Finally, in the case of a potential subsequent removal of the hip screw, a relatively great intervention is required to release the locking screw, screwed proximally into the intramedullary pin, in one step prior to removing the hip screw.

Furthermore, from U.S. Pat. No. 5,454,813 to Lawes, an intramedullary pin with a hip screw and a sliding sleeve is known, wherein the transition in the intramedullary pin, the external and internal profile of the sliding sleeve, and the shaft of the hip screw have a non-circular construction. Consequently, the sliding sleeve acts as an anti-rotational means between the hip screw and the intramedullary pin. This known device has the disadvantage that the prior introduced hip screw has to be rotated again one way or another during the assembly of the sliding sleeve, until it is so aligned that the non-circular cross-sections of the shaft, the external and internal profiles of the sliding sleeve and of the passage allow the introduction of the sliding sleeve. This means a time-consuming adjustment for the surgeon. A further disadvantage of this device is that a medial movement can be prevented only with an additional component (tension adjuster).

The purpose of the preceding discussion of the state-of-the-art is merely to explain the field of the invention and is not an admission that the state-of-the-art quoted has actually been published or is public knowledge at the time of this application.

SUMMARY OF THE INVENTION

This is where the invention wants to provide a remedy. The invention is based on the problem to produce a device for the treatment of bone fractures, particularly of proximal femoral fractures, that does not require elaborate adjusting steps by the surgeon during the implanting and allows a simply lockable and releasable form-locking locking of the rotation between the longitudinal bone fixing element (e.g., a hip screw or helical blade) and the intramedullary pin.

The invention achieves the objective set by a device for the treatment of femoral fractures comprising an intramedullary pin/nail having a central longitudinal axis, a distal portion configured and dimensioned for insertion into the medullary canal of a femur, a proximal portion, and a passage through the proximal portion, the passage having a non-circular cross-section and a central axis that forms a non-perpendicular angle with respect to the central longitudinal axis of the nail. A sliding sleeve is configured and dimensioned for insertion through the passage in the nail, the sleeve having a central longitudinal bore, a first end, a second end, an external jacket surface, and an internal jacket surface, where at least a portion of the external jacket surface of the sliding sleeve has a non-circular cross-section that mates with the non-circular cross-section of the passage to prevent rotation of the sliding sleeve with respect to the nail while permitting translation of the sliding sleeve with respect to the nail. A bone fixation element has a longitudinal axis, and includes a head portion configured and adapted to engage bone in the head of the femur, and a shaft portion configured and dimensioned for insertion into the central longitudinal bore of the sliding sleeve. The shaft portion of the bone fixation element is configured and adapted to be freely rotatable with respect to the sliding sleeve when in a first position and rotationally locked with respect to the sliding sleeve when in a second position.

The advantages achieved by the invention are essentially that as a result of the device according to the invention:

- the locking means permits the bone fixing element to be optionally locked and released relative to the intramedullary pin with regard to rotation about the longitudinal axis of the bone fixing element;
- the locking means can be locked and released laterally;
- due to the rotatability of the sliding sleeve on the shaft of the bone fixing element, the introduction of the sliding sleeve after the implanting of the bone fixing element is possible prior to the assembly without long adjustment of the sliding sleeve and consequently the operation will be simplified and shortened;
- the lateral sliding of the longitudinal bone fixing element is not limited by the locking means;
- the front portion of the longitudinal bone fixing element, preferably constructed as a screw or a helical blade, can be optimally anchored in the spongiosa of the femoral head because, during its introduction, the shaft of the longitudinal bone fixing element remains rotationally freely displaceable in the surrounding sleeve;
- during its introduction into the femoral head, the longitudinal bone fixing element does not need to be specially aligned and can rotate helically on impact in the femoral head. At this stage, the longitudinal bone fixing element is not yet secured against rotation. Thus the surgeon can rotationally correct the femoral head, before he locks the rotation of the longitudinal bone fixing element in the longitudinal bore of the sliding sleeve.

In a preferred embodiment, the locking means comprises a tightening screw, that is axially fixed, yet rotatably connected, with the shaft, by means of a bush that can be axially displaced in the longitudinal bore of the sliding sleeve and can rotate relative to the sliding sleeve. At the front end of the bush and at the free end of the shaft there are preferably means provided which can be engaged by rotation with one another in a form-locking manner.

In another embodiment the means at the front end of the bush and at the free end of the shaft are constructed as complementary spur gears. The following advantages are achieved by this:

- the spur gears allow an engagement between the bone fixing element and the sliding sleeve at various angles of rotation, so that a simple adjustment between the bone fixing element and the intramedullary pin is possible during the implantation; and
- by virtue of the spur gears a reliable securing against rotation can be achieved.

In yet another embodiment, at its front end, the tightening screw has an annular bead, while the shaft has a coaxial bore with an undercut accommodating the bead, so that the tightening screw is axially fixed, but rotatably connected with the shaft. The bore and the undercut preferably contain a radial opening, so that the tightening screw can be assembled transversely to the longitudinal axis of the bone fixing element.

In a further embodiment, the non-circular passage is complementary to the non-circular cross-section of the external jacket surface of the sliding sleeve, while the cross-section of the passage, for example, is so constructed that the non-circular cross-section of the passage has circumferential partial sections in the form of partial circular arcs.

In another preferred embodiment, the fixing means of the longitudinal bone fixing element is a helical blade, and preferably a double helical blade. Other embodiments of the fixing means may include a screw thread with a relatively fine pitch, a chisel, a pin, a T-section or a double T-section.

In another embodiment the head portion of the longitudinal bone fixing element is constructed as a multi-start thread, preferably as a four-start thread. Due to this configuration the positioning of the bone fixing element is of no consequence. At the same time the thread of the head portion can have a pitch of at least 50 mm, preferably at least 80 mm. The advantage of this relatively coarse pitch is the higher resistance against the rotation of the bone fixing element. In addition, the bone fixing element, constructed as a helical blade, causes less damage to the bony substance than a conventional hip screw with a relatively fine pitch of the thread. The bone is more compacted than cut by the helical surfaces of the helical blade.

The locking means are preferably so dimensioned, that they act as an axial stop with regard to the passage of the intramedullary pin. This stop prevents excessive medial movement of the bone fixing element.

In another embodiment, the longitudinal bone fixing element is a hip screw.

In yet another embodiment, the longitudinal bone fixing element is a helical blade.

BRIEF DESCRIPTION OF THE DRAWINGS

The invention and developments of the invention are explained in detail in the following based on partly schematic illustrations of several embodiments, wherein:

FIG. 1 shows a side view through a device according to a preferred embodiment of the present invention;

FIG. 2 shows a partial section through an intramedullary pin in the region of its oblique passage with the bone fixing element and sliding sleeve inserted;

FIG. 10 shows a longitudinal section through the embodiment of the sliding sleeve illustrated in FIG. 2;

FIG. 11 shows a rear view on the embodiment of the sliding sleeve illustrated in FIG. 10;

FIG. 12 shows a longitudinal section through the embodiment of the sliding sleeve illustrated in FIG. 2 with the shaft of the bone fixing element introduced; and FIG. 13 shows a section along line XIII-XIII of FIG. 12.

DETAILED DESCRIPTION OF THE PREFERRED EMBODIMENTS

Figure 3:
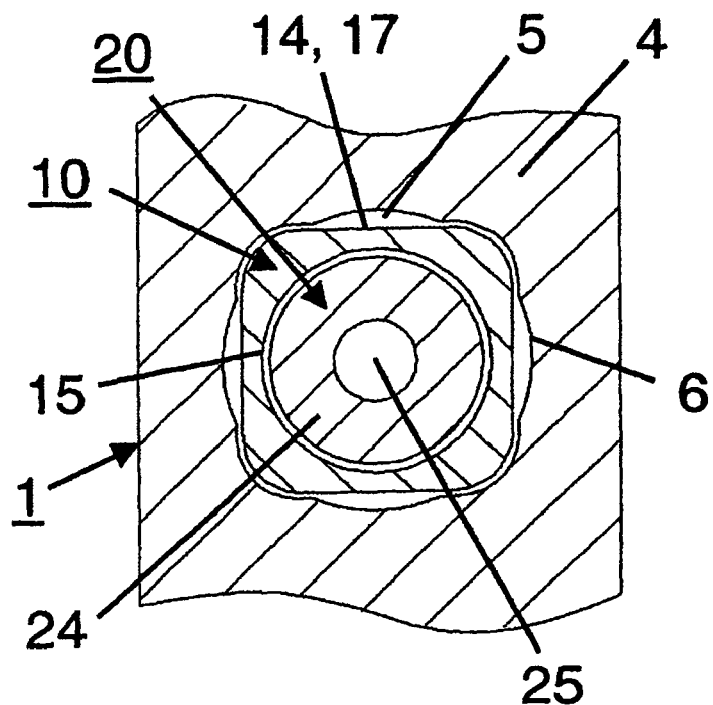
FIG. 3 shows a partial section through a modified intramedullary pin in the region of its oblique passage with the bone fixing element and sliding sleeve inserted.

In FIGS. 1-2, as well as FIGS. 5-8, a device for the treatment of femoral fractures is illustrated, that comprises an intramedullary pin 1, a sliding sleeve 10, a longitudinal bone fixing element 20 in the form of a hip screw or a helical blade, and a locking means 30. The intramedullary pin 1 has a central longitudinal axis 2, a front portion 3 that can be introduced into the medullary canal, a rear portion 4, as well as a passage 5 with a non-circular cross-section 6 (FIGS. 2-4) that passes through the rear portion 4 obliquely to the longitudinal axis 2. The sliding sleeve 10, that can pass through the non-circular passage 5, has a front end 11, a rear end 12, a central longitudinal bore 13, an external jacket surface 14, an internal jacket surface 15, as well as a longitudinal axis 16.

The longitudinal bone fixing element 20, in the form of a hip screw or helical blade, has a longitudinal axis 21, a head portion 22 with fixing means 23 in the form of a multi-start thread of relatively coarse pitch, that can engage the femoral head during use, as well as a shaft 24 that can be coaxially introduced into the sliding sleeve 10. The external jacket surface 14 of the sliding sleeve 10 has a non-circular cross-section 17, while the internal jacket surface 15 of the sliding sleeve 10 has a non-circular cross-section 38 only on its rear segment 36 adjoining its rear end 12, and a circular cross-section 18 on a front segment 37 (FIGS. 10, 11). The circular cross-section 18 of the front segment 37 (FIGS. 10, 11) has the same diameter as the shaft 24 of the bone fixing element 20, so that the bone fixing element 20 is mounted in the sliding sleeve 10 in an axially displaceable and rotatable manner about the longitudinal axis 16. A segment at the transition between this segment of the shaft 24, that can be introduced into the longitudinal bore 13, and the head portion 22 of the bone fixing element 20 has a larger diameter, so that by virtue of this a shoulder 39 is formed that can be brought to rest at the front end 11 of the sliding sleeve 10. The possibility of axial displacement of the bone fixing element 20 relative to the rear end 11 of the sliding sleeve 10 is limited by virtue of this shoulder 39. Finally locking means 30 are provided to enable the optional locking of the rotation of the bone fixing element in the sliding sleeve 10.

As illustrated in FIG. 2, the sliding sleeve 10 with a non-circular cross-section 17 of its external jacket surface 14 is secured against rotation in the passage 5 of the intramedullary pin 1 with equally non-circular cross-section 6. As also illustrated in FIG. 2, the non-circular cross-section 6 of the passage 5 is constructed essentially as a circle with two diametrically opposing ribs 7, which are parallel to the longitudinal axis 16 of the sliding sleeve 10. The sliding sleeve 10 is secured in the passage 5 against rotation relative to the intramedullary pin 1 by the complementary construction of the external jacket surface 14 of the sliding sleeve 10 with two protrusions 35. By virtue of this design, the intramedullary pin 1 can be also used with a conventional hip screw having a cylindrical shaft, i.e. without a sliding sleeve.

FIG. 3 illustrates a version of the non-circular cross-section 6 of the passage 5. The cylindrical shaft 24 of the longitudinal bone fixing element 20, constructed as a hip screw or helical blade, is mounted in a rotatable manner in the interior of the sliding sleeve 10 with a cylindrical internal jacket surface 15 in the front segment 37. In contrast to that, the external jacket surface 14 of the sliding sleeve 10, having an essentially quadratic, i.e. non-circular, cross-section 17, is secured against rotation in the passage 5 of the intramedullary pin 1 also having a non-circular cross-section 6. As FIG. 3 illustrates, the non-circular cross-section 6 of the passage 5 has also an approximately quadratic construction, but has additional peripheral part-sections in the form of partial circular arcs. Due to this construction, the intramedullary pin 1 can be also used with a conventional hip screw with a cylindrical shaft, i.e., without a sleeve.

Figure 4:
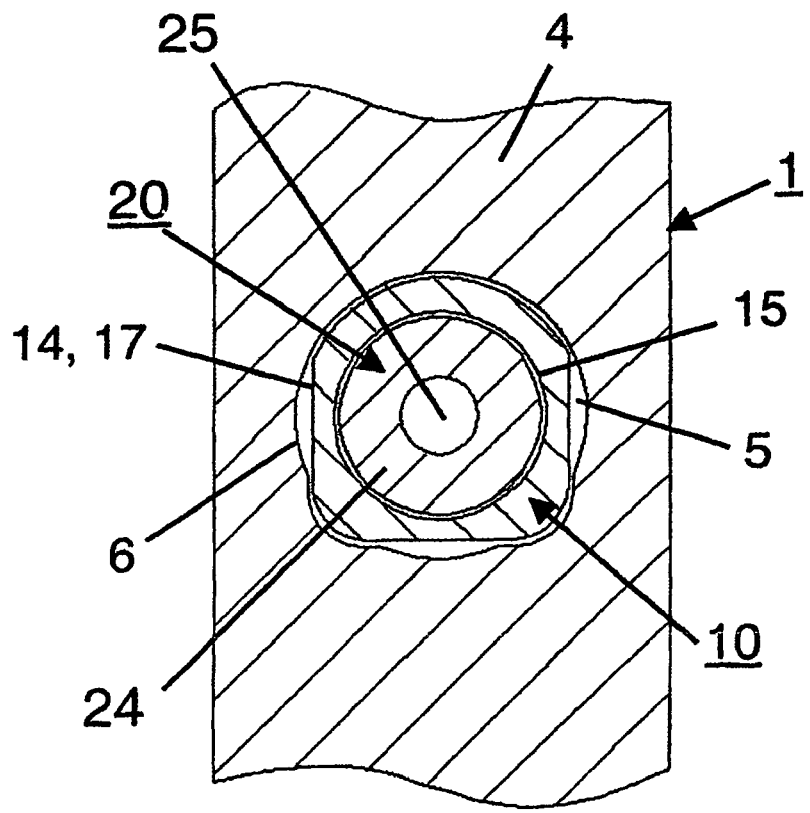
FIG. 4 shows a partial section through another modified intramedullary pin in the region of its oblique passage with the bone fixing element and sliding sleeve inserted.
Figure 5:
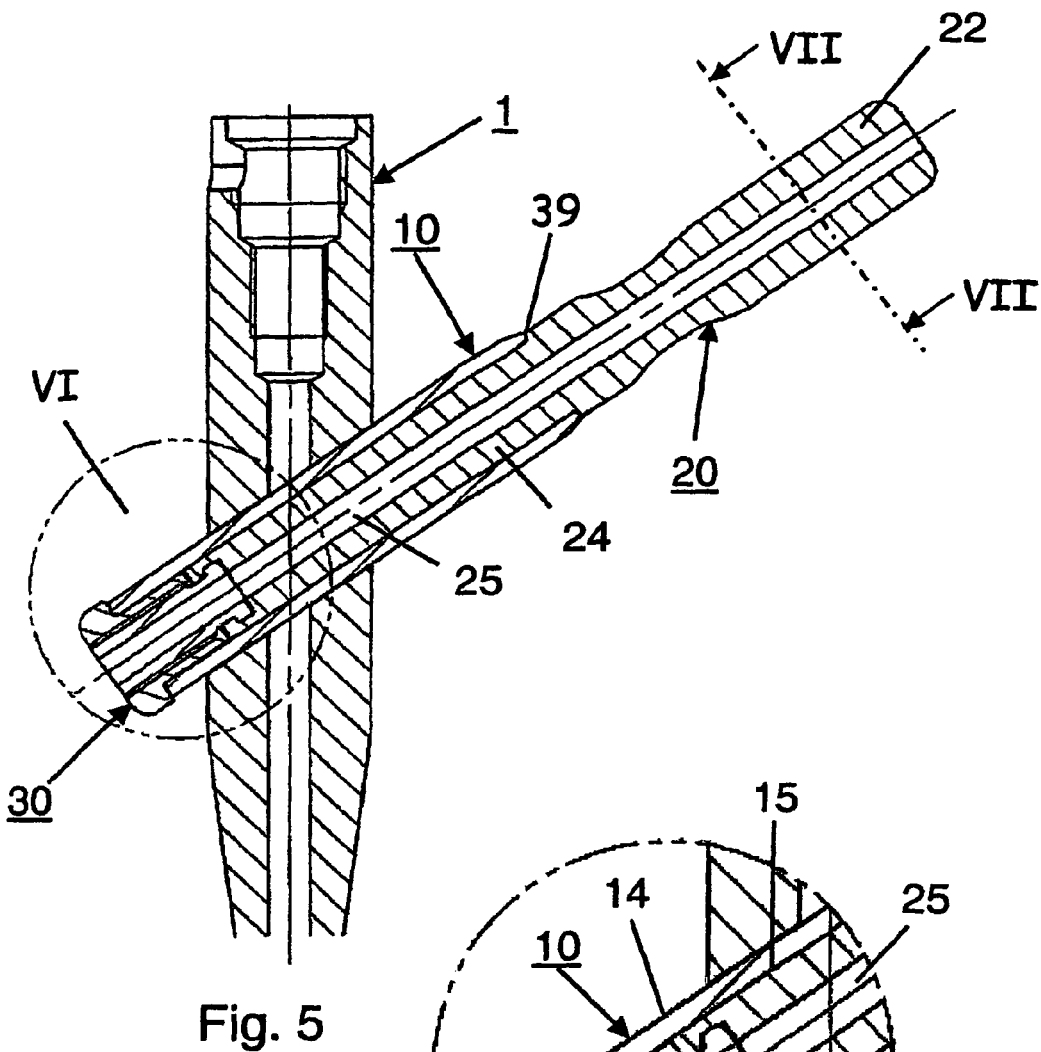
FIG. 5 shows a partial section through the device according to FIG. 1.
Figure 6:
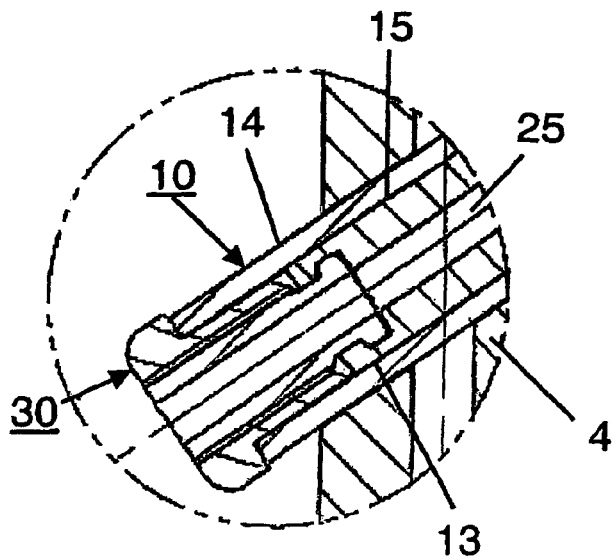
FIG. 6 shows an enlarged detail of the circle VI of FIG. 5.

FIG. 4 illustrates a further version of a non-circular cross-section 6 of the passage 5, wherein two small partial circular arcs and a larger partial circular arc are present. The non-circular cross-section 17 of the external jacket surface 14 of the sliding sleeve 10 is correspondingly constructed.

Figure 9A:
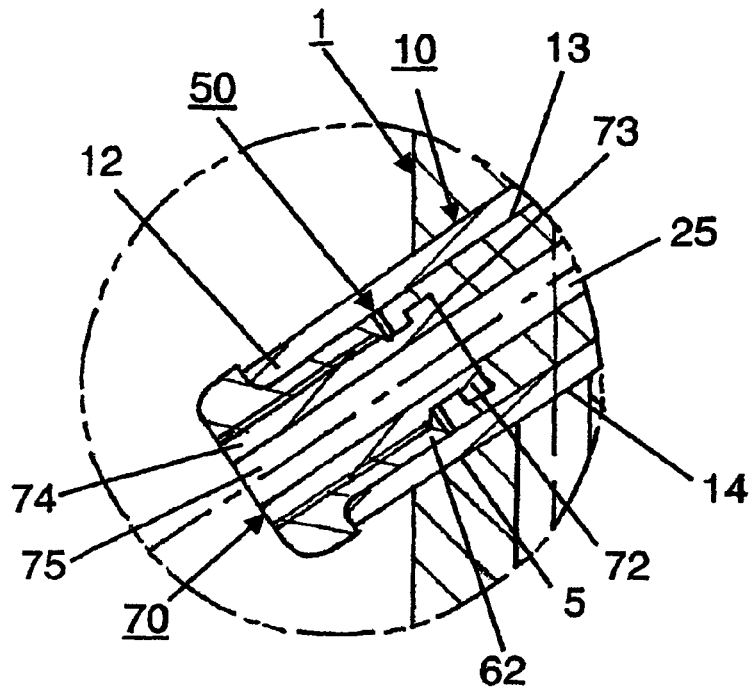
FIG. 9a shows an enlarged detail of the circle VI of FIG. 5 with the locking means locked.
Figure 9B:
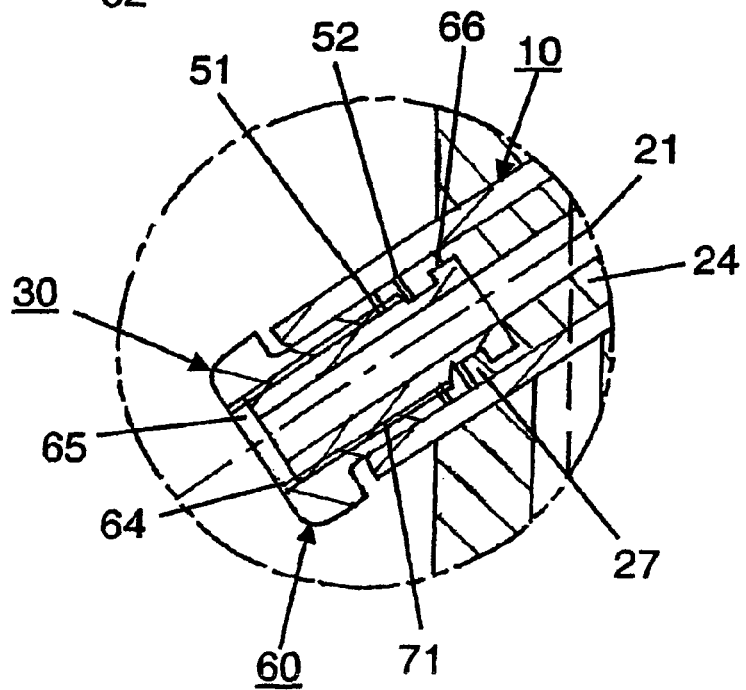
FIG. 9b shows an enlarged detail of the circle VI of FIG. 5 with the locking means released.

As it is illustrated in FIGS. 9a and 9b, the locking means 30 comprises a bush 60 that is displaceable parallel to the longitudinal axis 21 of the bone fixing element 20 as well as a tightening screw 70. At the rear end 12 of the sliding sleeve 10 the bush 60 is axially displaceably mounted in the longitudinal bore 13 of the sleeve.

As FIGS. 10 and 12 illustrate, the longitudinal bore 13 in the sliding sleeve 10 comprises two axially adjacent segments 36, 37, of which the front segment 37 has a circular cross-section 18. Therefore, when the locking means 30 (FIG. 9b) are released, the shaft 24 of the bone fixing element 20 is mounted in the sliding sleeve 10 rotatable about its longitudinal axis 16.

Figure 7:
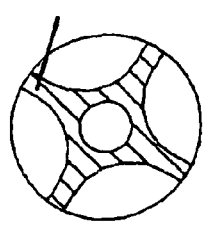
FIG. 7 shows a section along the line VII-VII of FIG. 5.
Figure 8:
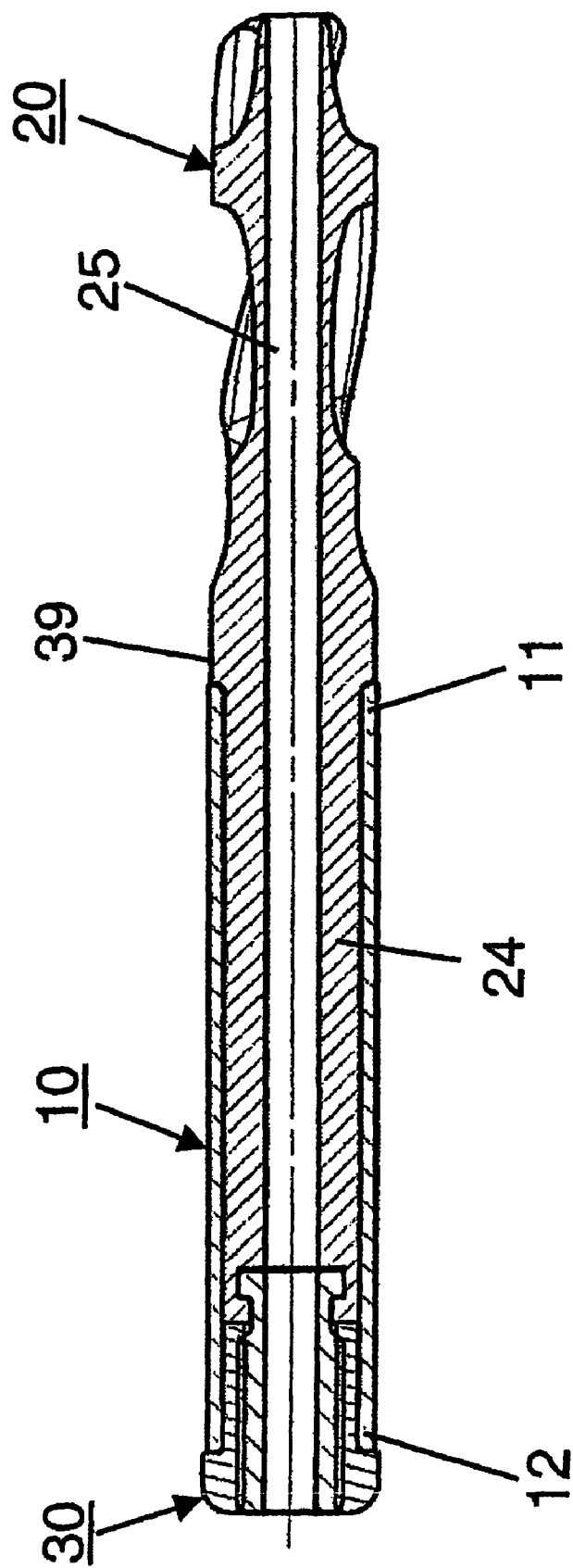
FIG. 8 shows a longitudinal section through the sliding sleeve with the bone fixing element pre-assembled therein.

As FIG. 7 illustrates, the fixing means 23 of the longitudinal bone fixing element 20 are constructed as a four-start helical blade, wherein the thread has a pitch of approx. 120 mm.

As FIGS. 9a and 9b illustrate, between the front end 62 of the bush 60 and the free end 27 of the shaft 24 means 50 are provided, which can be engaged by rotation with one another in a form-locking manner, said means can be engaged by axially displacing the bush 60. When the means 50 are engaged, i.e., locked (FIG. 9a), a relative rotation between the bush 60 and the shaft 24 about the longitudinal axis 21 of the bone fixing element 20 is prevented, whereas when the means are released (FIG. 9b) a rotation of the bone fixing element 20 relative to the sliding sleeve 10 is possible. The means 50 are constructed in this case as spur gears 51, 52, wherein on the front end 62 of the bush 60 an annular, first spur gear 51 is provided and the second spur gear 52 is also annular and is provided on the free end 27 of the shaft 24. The bush 60 has a central bore 65 with a coaxial inside thread 64, that can be screwed onto the outside thread 71 of the tightening screw 70. When the tightening screw 70 is tightened, the bush 60 is axially displaced towards the free end 27 of the shaft 24 until the two spur gears 51, 52 on the front end 62 of the bush 60 and on the free end 27 of the shaft 24 become engaged (FIG. 9a). By virtue of this, a relative rotation between the bush 60 and the shaft 24 about the longitudinal axis 21 of the bone fixing element 20 will be prevented. In the region of its rear segment 36 the longitudinal bore 13 has a non-circular cross-section 38 also with two flattenings 41 (FIG. 11). By virtue of the complementary non-circular cross-sections of the bush 60 and of the longitudinal bore 13 in the sliding sleeve 10 a rotation between the bush 60 and the sliding sleeve 10 is prevented.

When the locking means 30 (FIG. 9a) locked, the bone fixing element 20 is secured against rotation relative to the sliding sleeve 10 on the one hand, and, on the other, due to the non-circular cross-sections 6, 17 of the passage 5 and of the external jacket surface 14, the sliding sleeve 10 is secured against rotation relative to the intramedullary pin 1.

The tightening screw 70 is axially fixed, yet rotatably connected, with the free end 27 of the shaft 24. As shown in FIGS. 9a and 9b, this axial connection is realized by a bead 72 at the front end 73 of the tightening screw 70, which engages the undercut 66 in the bore 25 in the shaft 24. Since the undercut 66 extends over the entire circumference of the bore 25, the rotation of the tightening screw 70 relative to the shaft 24 about the longitudinal axis 21 of the bone fixing element 20 is not prevented. The tightening screw 70 has a coaxial bore passing through it and has at its rear end 74 means 75 to accept a screwdriver (not illustrated). By virtue of the axial fixing of the tightening screw 70 on the shaft 24, when the tightening screw 70 is tightened, the bush 60 is displaced towards the free end 27 of the shaft 24 until the two spur gears 51, 52 engage one another, whereas when the tightening screw 70 is released, the bush 60 is displaced in the opposite direction until the two spur gears 51, 52 become disengaged.

As it can be seen from FIGS. 12 and 13, in the region of the free end 27 of the shaft 24, the wall of the shaft 24 has a radial opening 42; as a matter of fact, in such a manner, the tightening screw 70 can be laterally introduced with the bead 72 into the undercut 66. This lateral introduction of the tightening screw 70 into the radial opening 42 is carried out before sliding the sliding sleeve 10 over the shaft 24. Finally, the tightening screw 70 is screwed into the inside thread 64 of the central bore 65 in the bush 60.

While the present invention has been described with reference to the preferred embodiments, those skilled in the art will recognize that numerous variations and modifications may be made without departing from the scope of the present invention. Accordingly, it should be clearly understood that the embodiments of the invention described above are not intended as limitations on the scope of the invention, which is defined only by the following claims.

What is claimed is:

1. A device for the treatment of femoral fractures comprising:
    an intramedullary nail having a central longitudinal axis, a proximal portion, a distal portion configured and dimensioned for insertion into the medullary canal of a femur, and a passage through the proximal portion, the passage having a non-circular cross-section and a central axis that forms a non-perpendicular angle with respect to the central longitudinal axis of the nail;
    a sliding sleeve configured and dimensioned for insertion through the passage in the nail, the sleeve having a central longitudinal bore, a first end, a second end, an external jacket surface, and an internal jacket surface, where at least a portion of the external jacket surface of the sliding sleeve has a non-circular cross-section that mates with the non-circular cross-section of the passage to prevent rotation of the sliding sleeve with respect to the nail while permitting translation of the sliding sleeve with respect to the nail; and a bone fixation element having a longitudinal axis, a head portion configured and adapted to engage bone in the head of the femur, and a shaft portion configured and dimensioned for insertion into the central longitudinal bore of the sliding sleeve, wherein the shaft portion of the bone fixation element is configured and adapted to be freely rotatable with respect to the sliding sleeve when received through the sliding sleeve in a first position and rotationally locked with respect to the sliding sleeve when received through the sliding sleeve in a second position.

2. The device of claim 1, further comprising a tightening screw at a free end of the shaft of the bone fixation element, the screw configured to rotate, but not axially translate, with respect to the shaft of the bone fixation element.

3. The device of claim 2, further comprising a bush at the first end of the sliding sleeve, the bush secured against rotation with respect to the longitudinal bore of the sliding sleeve but configured to axially translate with respect to the longitudinal bore of the sliding sleeve when engaged by the tightening screw on the shaft of the bone fixation element.

4. The device of claim 3, further comprising complementary locking structures at a first end of the bush and at the free end of the shaft of the bone fixation element, the locking structures preventing rotation of the shaft with respect to the bush when the free end of the shaft engages the first end of the bush.

5. The device of claim 4, wherein the complementary locking structures include a first spur gear on the first end of the bush and a second spur gear on the free end of the shaft of the bone fixation element.

6. The device of claim 3, wherein a portion of the internal jacket surface at the first end of the sliding sleeve has a non-circular cross-section that mates with an outer surface of the bush to prevent rotation of the bush relative to the longitudinal bore of the sliding sleeve.

7. The device of claim 3, wherein the bush limits axial translation of the sleeve through the passage of the nail.

8. The device of claim 2, wherein the tightening screw includes an annular bead that mates with an undercut in an axial bore of the shaft of the bone fixation element to permit rotation of the screw with respect to the shaft while preventing axial translation of the screw relative to the shaft.

9. The device of claim 8, further comprising a radial opening in the axial bore and the undercut which permits connection of the tightening screw with the shaft of the bone fixing element.

10. The device of claim 1, wherein the head portion of the bone fixation element includes at least two helical blades.

11. The device of claim 10, wherein the pitch of the helical blades on the bone fixation element is at least 50 mm.

12. The device of claim 1, wherein the non-circular cross-section of the passage in the nail includes circumferential partial sections in the form of partial circular arcs.

13. The device of claim 1, wherein the head portion of the bone fixation element includes a screw thread, a chisel, a pin, a T-section or a double T-section.

14. A device for the treatment of femoral fractures comprising:

an intramedullary nail having a central longitudinal axis, a distal portion configured and dimensioned for insertion into the medullary canal of a femur, a proximal portion, and a passage through the proximal portion, the passage fanning an oblique angle with respect to the central longitudinal axis of the nail;

a sliding sleeve configured and dimensioned for insertion through the passage in the nail, the sleeve having a central longitudinal bore, a first end, a second end, an external jacket surface, and an internal jacket surface, where at least a portion of the external jacket surface of the sliding sleeve and the passage are configured and adapted to prevent rotation of the sliding sleeve with respect to the nail while permitting translation of the sliding sleeve with respect to the nail; and a bone fixation element having a longitudinal axis, a bone engaging portion, and a shaft portion configured and dimensioned for insertion into the central longitudinal bore of the sliding sleeve, wherein the shaft portion of the bone fixation element is configured and adapted to be freely rotatable with respect to the sliding sleeve when received through the sliding sleeve in a first position and rotationally locked with respect to the sliding sleeve when received through the sliding sleeve in a second position.

15. The device of claim 14, further comprising a tightening screw at a free end of the shaft of the bone fixation element, the screw configured to rotate, but not axially translate, with respect to the shaft of the bone fixation element.

16. The device of claim 15, further comprising a bush at the first end of the sliding sleeve, the bush secured against rotation but configured to axially translate with respect to the longitudinal bore of the sliding sleeve when engaged by the tightening screw on the shaft of the bone fixation element.

17. The device of claim 16, further comprising complementary locking structures at a first end of the bush and at the free end of the shaft of the bone fixation element, the locking structures preventing rotation of the shaft with respect to the bush when the free end of the shaft engages the first end of the bush.

18. The device of claim 17, wherein the complementary locking structures further comprise a first spur gear on the first end of the bush and a second spur gear on the free end of the shaft of the bone fixation element.

19. A method for treating femoral fractures comprising the steps of:

inserting a first intramedullary implant into the marrow canal of the femur, the first implant having a central longitudinal axis, a distal portion configured and dimensioned for insertion into the medullary canal, a proximal portion, and a passage through the proximal portion, the passage having a non-circular cross-section and a central axis that forms a non-perpendicular angle with respect to the central longitudinal axis of the first implant;

inserting a second implant through the passage in the first implant to engage bone in the femoral head, the second implant including a sliding sleeve configured and dimensioned for insertion through the passage in the first implant, the sleeve having a central longitudinal bore, and an external jacket surface, where at least a portion of the external jacket surface of the sliding sleeve is configured and adapted to prevent rotation of the sliding sleeve with respect to the first implant while permitting translation of the sliding sleeve with respect to the first implant, and a bone fixation element having a longitudinal axis, a head portion configured and adapted to engage bone in the head of the femur, and a shaft portion configured and dimensioned for insertion into the central longitudinal bore of the sliding sleeve, wherein the shaft portion of the bone fixation element is configured and adapted to be freely rotatable with respect to the sliding sleeve when received through the sliding sleeve in a first position and rotationally locked with respect to the sliding sleeve when received through the sliding sleeve in a second position; and moving the shaft portion of the bone fixation element into the second position to prevent rotation of the bone fixation element with respect to the first implant.

20. The method of claim 19, wherein the second implant further includes a tightening screw at a free end of the shaft of the bone fixation element, the screw configured to rotate, but not axially translate, with respect to the shaft of the bone fixation element; and a bush at a first end of the sliding sleeve, the bush configured to axially translate, but not rotate, with respect to the longitudinal bore of the sliding sleeve when engaged by the tightening screw on the shaft of the bone fixation element.

* * * * *